(12) United States Patent
Horoshutin

(10) Patent No.: US 11,097,080 B2
(45) Date of Patent: Aug. 24, 2021

(54) CLASSICAL CONDITIONING TOOL KIT FOR ATTITUDE CHANGE USED IN THE PROVISION OF PSYCHOLOGICAL SUPPORT

(71) Applicant: Pavel Pavlovich Horoshutin, Irkutsk (RU)

(72) Inventor: Pavel Pavlovich Horoshutin, Irkutsk (RU)

( * ) Notice: Subject to any disclaimer, the term of this patent is extended or adjusted under 35 U.S.C. 154(b) by 316 days.

(21) Appl. No.: 16/320,098

(22) PCT Filed: Jan. 11, 2017

(86) PCT No.: PCT/RU2017/000007
§ 371 (c)(1),
(2) Date: Jan. 24, 2019

(87) PCT Pub. No.: WO2018/034590
PCT Pub. Date: Feb. 22, 2018

(65) Prior Publication Data
US 2019/0269882 A1 Sep. 5, 2019

(30) Foreign Application Priority Data
Aug. 16, 2016 (RU) .......................... RU2016133477

(51) Int. Cl.
*A61M 21/02* (2006.01)
*A61M 21/00* (2006.01)

(52) U.S. Cl.
CPC ............ *A61M 21/02* (2013.01); *A61M 21/00* (2013.01); *A61M 2021/005* (2013.01); *A61M 2021/0016* (2013.01); *A61M 2021/0027* (2013.01); *A61M 2021/0077* (2013.01); *A61M 2205/58* (2013.01)

(58) Field of Classification Search
CPC .............................. A61M 21/00; A61M 21/02
See application file for complete search history.

(56) References Cited

U.S. PATENT DOCUMENTS

| 2019/0151603 A1* | 5/2019 | Horoshutin | ............ A61B 5/165 |
| 2019/0236977 A1* | 8/2019 | Horoshutin | ............ G09B 5/065 |

FOREIGN PATENT DOCUMENTS

| RU | 99123287 A | 8/2001 |
| RU | 2315633 C1 | 1/2008 |
| RU | 2010108361 A | 9/2011 |
| RU | 2590860 C2 | 7/2016 |

OTHER PUBLICATIONS

Baillon S. et al. Multi-sensory therapy in psychiatric care. Advances in Psychiatric Treatment, vol. 8, 2002, pp. 444-452.
Malkina-Pykh I. G. Psikhosomatika. Spravochnik prakticheskogo psikhologa. M., 2008, p. 102, 217.

* cited by examiner

*Primary Examiner* — John P Lacyk
(74) *Attorney, Agent, or Firm* — Georgiy L. Khayet

(57) ABSTRACT

The invention relates to psychology and is used in psychological correction of mental states and dependencies and correction of social behavior in methods aimed at attitude change. Provided is a classical conditioning tool kit for changing problematic attitude to positive attitude while providing psychological support by using tools of pleasant classical conditioning affecting all sensory channels of information perception of a human. The kit includes at least one flavoring food additive, at least one aromatic essential oil, at least one mineral, auto-training text for audio listening, and an image with a suggestive formula to change a problematic attitude to a positive attitude. One image with a selected suggestive formula for changing the attitude includes one or more linguistic phrases targeting kinesthetic sensations, and another image includes linguistic persuasions that assist with forming a new attitude. All tools evoke pleasant feelings in a patient.

18 Claims, No Drawings

CLASSICAL CONDITIONING TOOL KIT FOR ATTITUDE CHANGE USED IN THE PROVISION OF PSYCHOLOGICAL SUPPORT

CROSS-REFERENCE TO RELATED APPLICATION

This application is a 371 application of international application No. PCT/RU2017/000007, entitled "CLASSICAL CONDITIONING TOOL KIT FOR ATTITUDE CHANGE USED IN THE PROVISION OF PSYCHOLOGICAL SUPPORT," filed on Jan. 11, 2017, which claims priority to patent application of the Russian Federation No. 2016/133477, filed on Aug. 16, 2016. The aforementioned applications are incorporated herein by reference in their entirety for all purposes.

TECHNICAL FIELD

The invention relates to the field of psychology and is used in psychological correction of mental states and dependencies, correction of social behavior in methods aimed at attitude change.

BACKGROUND

Known are various methods for correction of mental states and dependencies, in which a psychologist tests a patient to determine individual characteristics of the human sensory perception system. By doing so, sensory preferences of the patient are determined, namely tools that evoke pleasant feelings. A kit of these tools is provided to maximize the involvement of the human sensory perception system in the process of changing the attitude and, consequently, increase the effectiveness of the process of providing psychological support.

For example, see the invention description of document No. RU2180242, published in 2002, A61M 21/00, which characterizes a tool kit for attitude change when providing psychological support and comprises the following set of essential features: an aromatic medallion with aromatic agents, for example, essential oil of peroli and/or rose and/or sandalwood and/or lavender; musical compositions, for example, works of L. Beethoven and/or C. Saint-Saens.

In the known technical solution, the tool kit is used as a method of providing a therapeutic action for two sensory channels of information perception, namely the olfactory sensory channel and the auditory sensory channel.

Furthermore, known is patent No. RU2315633, published in 2008, A61M 21/00, the description of which characterizes a tool kit consisting of a color picture, an aroma lamp with essential oils, and musical compositions.

In the known technical solution, the tool kit is used as a method of providing a therapeutic action in the method for three sensory channels of information perception, namely for the olfactory sensory channel, the auditory sensory channel, and the visual sensory channel.

The closest analogue, i.e. the prototype, is considered to be a tool kit for changing problematic attitude to positive attitude when providing psychological support, which is characterized in patent No. RU2590860, published in 2016, A61M 21/00, and comprises flavoring food additives, aromatic essential oils, minerals with varying thermal conductivity, autogenic training text for audio listening, and a picture with a chosen suggestive formula.

The prototype uses the tool kit to change the attitude for five sensory channels of information perception, namely the olfactory, auditory, visual, tactile, and gustatory sensory channels. In the prototype, the tools are used to as stimuli of sensory channels of perception.

DETAILED DESCRIPTION

The problem of creating the classical conditioning tool kit for changing problematic attitude to positive attitude when providing psychological support is to systematize the process of classical conditioning and enhance its effectiveness.

The technical effect is using tools for the purposes of classical conditioning and for involving the entire human sensory system of perception into the process of autogenic training.

The technical effect is achieved by the fact that the classical conditioning tool kit for changing problematic attitude to positive attitude while providing psychological support includes at least one flavoring food additive, at least one aromatic essential oil, at least one mineral, autogenic training text for audio listening, an image with a suggestive formula to change the problematic attitude to the positive attitude, in which one image with a chosen suggestive formula for changing the attitude includes one or more linguistic phrases targeted at kinaesthetic sensations, and the second image includes a formula consisting of linguistic persuasions that form new attitude, and all tools evoke pleasant feelings in a patient.

The tools are combined into a single package. The tool kit contains an instruction for use of tools included in the tool kit. The tool kit contains an accessory for using the aromatic essential oil.

The proposed tool kit is used for the pleasant classical conditioning, which is carried out through all sensory channels of information perception of a human, namely a visual, auditory, tactile, olfactory, gustatory, reasoning and kinaesthetic channel. The whole sensory system of human perception is involved in the process of autogenic training and the principle of maximum efficiency of classical conditioning is implemented.

In the course of the correction of mental states and dependencies, a psychologist tests the patient to determine individual characteristics of the human sensory system of perception, thereby ascertaining the sensory preferences of the patient, namely tools evoking pleasant feelings through seven information perception sensory channels. The obtained information is used to develop a process of full-sensory pleasant classical conditioning. To implement this process and involve it in the process of attitude change, for example, the following tool kit is proposed.

A kit of essential oils and an accessory for their use, for example, an aroma lamp. Essential oils are selected by the patient during psychodiagnostics and are used to create a persistent aroma in the room. This tool creates a pleasant feeling through the olfactory sensory channel of information perception.

The autogenic training text and audio player for text listening. The text is recorded using the audio player by the voice of the patient by the patient himself and is then listened to, for example, daily. It creates a pleasant feeling through the auditory sensory channel of information perception.

The image with a chosen suggestive formula to change the attitude is an image made according to a design determined based on the psychodiagnostics, with key linguistic phrases of the suggestive formula. The patient chooses a particular image, as well as color and text font, which are the most pleasant to him, by himself, during the psychodiagnostics. The suggestive formula is one or more linguistic phrases that form a new attitude. This tool includes the visual sensory channel of information perception into the autogenic training process.

An image with a formula of kinaesthetic sensations. It is an image made according to a design determined based on the psychodiagnostics and including one or more linguistic phrases targeting kinaesthetic sensations, the character of which is also determined during the testing. The patient chooses a particular image, as well as a color and text font, which are the most pleasant to him, by himself during the psychodiagnostics. It creates pleasant feelings through the kinaesthetic sensory channel of information perception. It includes the kinaesthetic sensory channel of information perception into the autogenic training process.

An image with a formula of linguistic persuasions. It is an image made according to a design determined based on the psychodiagnostics. The patient selects the design by himself during the psychodiagnostics. It is based on linguistic phrases, which are also formed based on tests and focus the attention of the patient during the autogenic training on pleasant reasoning conclusions. It creates pleasant feelings through the reasoning sensory channel of information perception. It includes the reasoning sensory channel of information perception into the autogenic training process.

A food additive having a strong taste. It is a food additive pleasant for the patient, for example, lollipops, which cause a long pleasant taste effect. It is determined during the psychodiagnostics. It is used by the patient while listening to the text of autogenic training. It creates pleasant feelings through the gustatory sensory channel.

Minerals providing various tactile sensations. They are minerals of various shapes. The patient selects the minerals during the psychodiagnostics. The minerals are held by the patient in his hand while listening to the text of autogenic training. They create a pleasant feeling through the tactile sensory channel of information perception.

An instruction for use of tools is a text explaining the order of application of the whole tool kit during the autogenic training.

Examples of the use of the tool kit for different mental states and dependencies and during the change of a social behavior.

An example of the use of the proposed kit in the psychological correction of states.

The patient is a woman, 38 years old, being aggressive in relations with a 14-year-old son. A remote testing method was used to diagnose the attitude, which is the cause of the aggressive behavior. The psychodiagnostics of the sensory perception system and the diagnostics of sensory preferences were carried out. For each sensory perception system, tools for the pleasant classical conditioning were selected. The text of the autogenic training to change the problematic attitude to the positive attitude was drafted. A tool kit for full-sensory classical conditioning was assembled and provided to the patient. The course of autogenic training with the help of the tool kit for full-sensory classical conditioning lasted 10 days, after which significant improvement in the mental state of the patient occurred.

An example of the use of the proposed tool kit in case of mental dependencies.

The patient is a man, 45 years old. The reason for applying for help is being overweight. The psychodiagnostics of the patient behavior was carried out and the attitudes defining the behavior associated with chronic overeating were determined. The text of the autogenic training for changing the problematic overeating attitudes to moderate nutrition attitudes and active lifestyle was drafted. The psychodiagnostics of the sensory perception system was carried out and sensory preferences of the patients were determined. Based on the diagnostics data, a tool kit for the full-sensory classical conditioning for the autogenic training process was assembled. The patient read the instructions by himself and passed the autogenic training course. The course lasted for 36 days. The weight has decreased by 8 kg. The patient managed to stop overeating and started the active lifestyle with daily walks and excursions on the weekends.

An example of using the tool kit for changing social behavior.

The parents of a teenager, 13 years old, applied for help. The reason of applying for help was the antisocial behavior associated with conflicts at school. The testing method was used to perform the psychodiagnostics, and the problem behavior attitudes were determined. The text of the autogenic training for changing the problematic attitudes to positive ones was drafted. The diagnostics of the sensory perception system was carried out and sensory preferences of the patients were determined. Based on the diagnostics, a tool kit for full-sensory classical conditioning was assembled and provided to the parents of the teenager. The autogenic training course lasted for 16 days. A sharp decrease in conflict situations at school was noted.

The invention claimed is:

1. A classical conditioning tool kit for changing a problematic attitude to a positive attitude while providing psychological support to a patient, the tool kit comprising a plurality of tools, the plurality of tools including:
    at least one flavoring food additive;
    at least one aromatic essential oil;
    at least one mineral;
    an autogenic training text for audio listening; and
    one or more images with a suggestive formula for changing the problematic attitude to the positive attitude, wherein the one or more images include:
        a first image, wherein the suggestive formula of the first image includes one or more linguistic phrases forming the positive attitude, the first image stimulating a visual sensory channel of information perception of the patient;
        a second image, wherein the suggestive formula of the second image includes one or more linguistic phrases targeting kinaesthetic sensations, the second image stimulating a kinaesthetic sensory channel of information perception of the patient; and
        a third image, wherein the suggestive formula of the third image includes one or more linguistic persuasions, the third image stimulating a reasoning sensory channel of information perception of the patient;
    wherein each of the plurality of tools is being selected by the patient to evoke pleasant feelings in the patient through sensory channels of the patient.

2. The tool kit of claim 1, wherein the plurality of tools is combined into a single package.

3. The tool kit of claim 1, further comprising an instruction for use of the plurality of tools.

4. The tool kit of claim 3, wherein the instruction prompts the patient to use the plurality of tools to perform the following actions:
    apply the at least one aromatic essential oil to create a persistent aroma in a room in which the patient is present;

taste the at least one flavoring food additive;
listen to the autogenic training text;
hold the at least one mineral in a hand of the patient; and
look at the one or more images,
wherein one or more of the actions are performed simultaneously.

5. The tool kit of claim 1, further comprising an accessory for using the at least one aromatic essential oil.

6. The tool kit of claim 1, wherein one or more of the at least one flavoring food additive, the at least one aromatic essential oil, the at least one mineral, the autogenic training text for audio listening, and one or more images are selected by the patient during psychodiagnostics provided to the patient.

7. The tool kit of claim 6, wherein the psychodiagnostics includes testing the patient to determine individual characteristics of a sensory system of information perception of the patient and ascertain sensory preferences of the patient, wherein the plurality of tools are selected based on the individual characteristics and the sensory preferences.

8. The tool kit of claim 7, wherein the at least one flavoring food additive is selected to evoke the pleasant feelings in the patient through a gustatory sensory channel of the sensory system, the at least one aromatic essential oil is selected to evoke the pleasant feelings in the patient through an olfactory sensory channel of the sensory system, the at least one mineral is selected to evoke the pleasant feelings in the patient through a tactile sensory channel of the sensory system, the autogenic training text for audio listening is selected to evoke the pleasant feelings in the patient through an auditory sensory channel of the sensory system, and one or more images are selected to evoke the pleasant feelings in the patient through one or more of a visual sensory channel, a reasoning sensory channel, and a kinaesthetic sensory channel of the sensory system.

9. The tool kit of claim 1, wherein the autogenic training text for audio listening is recoded by the patient using a voice of the patient.

10. A method for creating a classical conditioning tool kit for changing a problematic attitude to a positive attitude while providing psychological support to a patient, the method comprising providing a plurality of tools, wherein the providing the plurality of tools includes:
providing at least one flavoring food additive;
providing at least one aromatic essential oil;
providing at least one mineral;
providing an autogenic training text for audio listening; and
providing one or more images with a suggestive formula for changing the problematic attitude to the positive attitude, wherein the one or more images include:
a first image, wherein the suggestive formula of the first image includes one or more linguistic phrases forming the positive attitude, the first image stimulating a visual sensory channel of information perception of the patient;
a second image, wherein the suggestive formula of the second image includes one or more linguistic phrases targeted at kinaesthetic sensations, the second image stimulating a kinaesthetic sensory channel of information perception of the patient; and
a third image, wherein the suggestive formula of the third image includes one or more linguistic persuasions, the third image stimulating a reasoning sensory channel of information perception of the patient;
wherein each of the plurality of tools is being selected by the patient to evoke pleasant feelings in the patient through sensory channels of the patient.

11. The method of claim 10, further comprising combining the plurality of tools into a single package.

12. The method of claim 10, further comprising providing an instruction for use of the plurality of tools.

13. The method of claim 10, further comprising providing an accessory for using the at least one aromatic essential oil.

14. The method of claim 10, further comprising selecting one or more of the at least one flavoring food additive, the at least one aromatic essential oil, the at least one mineral, the autogenic training text for audio listening, and one or more images by the patient during psychodiagnostics provided to the patient.

15. The method of claim 14, further comprising providing the psychodiagnostics to the patient, wherein the providing the psychodiagnostics includes testing the patient to determine individual characteristics of a sensory system of information perception of the patient and ascertaining sensory preferences of the patient, wherein the plurality of tools is selected based on the individual characteristics and the sensory preferences.

16. The method of claim 15, wherein the at least one flavoring food additive is selected to evoke the pleasant feelings in the patient through a gustatory sensory channel of the sensory system, the at least one aromatic essential oil is selected to evoke the pleasant feelings in the patient through an olfactory sensory channel of the sensory system, the at least one mineral is selected to evoke the pleasant feelings in the patient through a tactile sensory channel of the sensory system, the autogenic training text for audio listening is selected to evoke the pleasant feelings in the patient through an auditory sensory channel of the sensory system, and one or more images are selected to evoke the pleasant feelings in the patient through one or more of a visual sensory channel, a reasoning sensory channel, and a kinaesthetic sensory channel of the sensory system.

17. The method of claim 10, wherein the autogenic training text for audio listening is recoded by the patient using a voice of the patient.

18. A classical conditioning tool kit for changing a problematic attitude to a positive attitude while providing psychological support to a patient, the tool kit comprising a plurality of tools, the plurality of tools including:
at least one flavoring food additive;
at least one aromatic essential oil;
at least one mineral;
an autogenic training text for audio listening; and
one or more images with a suggestive formula for changing the problematic attitude to the positive attitude, wherein the one or more images include at least one of the following images:
a first image, wherein the suggestive formula of the first image includes one or more linguistic phrases forming the positive attitude, wherein the first image includes a visual sensory channel of information perception of the patient;
a second image, wherein the suggestive formula of the second image includes one or more linguistic phrases targeted at kinaesthetic sensations, and wherein the second image includes a kinaesthetic sensory channel of information perception of the patient; and
a third image, wherein the suggestive formula of the second image includes one or more linguistic persuasions, and wherein the third image includes a reasoning sensory channel of information perception of the patient;

wherein each of the plurality of tools being selected by the patient to evoke pleasant feelings in the patient through sensory channels of the patient, wherein the at least one flavoring food additive is selected to evoke the pleasant feelings in the patient through a gustatory sensory channel of a sensory system of the patient, the at least one aromatic essential oil is selected to evoke the pleasant feelings in the patient through an olfactory sensory channel of the sensory system, the at least one mineral is selected to evoke the pleasant feelings in the patient through a tactile sensory channel of the sensory system, the autogenic training text for audio listening is selected to evoke the pleasant feelings in the patient through an auditory sensory channel of the sensory system, and one or more images are selected to evoke the pleasant feelings in the patient through one or more of a visual sensory channel, a reasoning sensory channel, and a kinaesthetic sensory channel of the sensory system.

* * * * *